United States Patent [19]
Taicher et al.

[11] Patent Number: 5,109,853
[45] Date of Patent: May 5, 1992

[54] REMOTE TEMPERATURE MONITORING APPARATUS AND TECHNIQUE

[75] Inventors: Zvi Taicher, 25 Ben Yehuda Street; Mordechai Shporer, both of Rehovot, Israel

[73] Assignee: Zvi Taicher, Rehovot, Israel

[21] Appl. No.: 631,746

[22] Filed: Dec. 20, 1990

Related U.S. Application Data

[63] Continuation of Ser. No. 299,966, Jan. 19, 1989, abandoned.

[30] Foreign Application Priority Data

May 23, 1988 [IL] Israel .................................... 86470

[51] Int. Cl.$^5$ ............................................ A61B 5/055
[52] U.S. Cl. ................................ 128/653.2; 128/736; 324/315
[58] Field of Search ................... 128/653 A, 736, 804; 324/315; 600/10, 12

[56] References Cited

U.S. PATENT DOCUMENTS

| | | |
|---|---|---|
| 4,138,998 | 2/1979 | Nowogrodzki . |
| 4,246,784 | 1/1981 | Bowen ............................... 128/736 |
| 4,385,634 | 5/1983 | Bowen ............................... 128/653 |
| 4,441,486 | 4/1984 | Pounds ............................. 128/24 A |
| 4,531,526 | 7/1985 | Genest ................................ 128/630 |
| 4,554,925 | 11/1985 | Young ................................ 128/653 |
| 4,558,279 | 12/1985 | Ackerman et al. .................. 324/315 |
| 4,608,994 | 9/1986 | Ozawa et al. ....................... 128/670 |
| 4,651,750 | 3/1987 | Northeved .......................... 128/736 |
| 4,709,701 | 12/1987 | Weber ................................ 128/804 |
| 4,712,560 | 12/1987 | Schaefer et al. .................... 128/653 |
| 4,815,479 | 3/1989 | Carr .................................. 128/804 |

FOREIGN PATENT DOCUMENTS

| | | |
|---|---|---|
| 0095124 | 11/1983 | European Pat. Off. ............ 128/653 |
| 3241009 | 5/1984 | Fed. Rep. of Germany ...... 128/736 |
| 8215200 | 9/1982 | France . |
| 2532751 | 3/1984 | France ............................... 128/736 |

OTHER PUBLICATIONS

Bubkov, Lotfullin, Majera, and Ruguslavskii, "Pulsed NOR Thermometer for Temperatures up to 870° K.", Izvestiva Akademii Nank SSSR, Seria F. Z. Cheskaya, vol. 39, No. 12, 1975, pp. 2655–2660.

Utton and Vanier, "Thermometry by Nuclear Quadrupole Resonance", Instrumentation Technology, Dec. 1976, pp. 47–52.

Ohte and Iwaaka, "A New Nuclear Quadropole Resonance Standard Thermometer", American Institute of Physics, 1982, pp. 1173–1180.

Ogawa and Morimoto, "Nuclear Magnetic Resonance of Fe$^{57}$ in Various Ferromagnetic Oxides", Journal of the Physical Society of Japan, vol. 17, No. 4, Apr. 1962, pp. 654–659.

Samaras and Cheung, "Microwave Hyperthermia for Cancer Therapy", CRC Critical Reviews in Bioengineering, Feb. 1981, pp. 123–184.

Vaguine, Christensen, Lindley, and Walston, "Multiple Sensor Optical Thermometry System for Application in Clinical Hyperthermia", IEEE Transactions on Biomedical Engineering, vol. BME-31, No. 1, pp. 168–172.

Cetas, "Will Thermometric Tomography Become Practical for Hyperthermia Treatment Monitoring?", Cancer Research (Suppl.) 44, Oct. 1984, pp. 4805s–4808s.

Parker, "Applications of NMR Imaging in Hyperthermia: An Evaluation of the Potential for Localized Tissue Heating and Noninvasive Temperature Monitoring", IEEE Transactions on Biomedical Engineering, vol. BME-31, No. 1, Jan. 1984, pp. 161–167.

(List continued on next page.)

*Primary Examiner*—Ruth S. Smith
*Attorney, Agent, or Firm*—Abelman, Frayne and Schwab

[57] ABSTRACT

A thermometry system comprising an implantable element having temperature dependent NMR properties, apparatus for applying an RF field to the implantable element, and apparatus for sensing the temperature dependent NMR response of the implantable element and for providing an output indication of temperature of the implantable element.

9 Claims, 2 Drawing Sheets

OTHER PUBLICATIONS

Petersson, Saaf, Bolmsio, and Persson, "Temperature Mapping Using an Ultra Lowfield MR Scanner", Sixth Annual Meeting of Society of Magnetic Resonance in Medicine, Aug. 17-21, 1987, New York City, U.S.A.

Morrish, A. (John Wiley & Sons), "The Physical Principles of Magnetism", p. 560.

P. Roschmann & K. M. Ludeke (A Ferrimagnetic Resonance Sensor for Remote Wireless Temperature Measurements in Organic Tissue, IEEE MTTS Digest, 1983).

Parker, D. L., et al., Temperature Distribution Measurements in Two-Dimensional NMR Imaging, Medical Physics, 10, 3, 1985, pp. 321-325.

Beckman, F. K., et al., Remote Temperature Sensing in Organic Tissue by Ferrimagnetic Resonance Frequency Measurements, In Conference Proceedings, 11th European Microwave Conference, Sep. 1981, pp. 433-437.

C. Kittel, p. 499 "Introduction to Solid State Physics", John Wiley & Sons.

McGraw-Hill Encyclopedia of Physics, pp. 601-604.

Gonano et al. (Sublattice Magnetization in Yttrium and Lutetium Iron Garnets) Physical Review, vol. 156(2), 521 (1967).

Myers et al. (Sublattice Magnetization of Several Rare Earth Iron Garnets) Physical Review, vol. 170 (2), 513 (1968)).

S. Chikazumi and S. Charap (John Wiley & Sons), Table 21.3 in "Physics of Magnetism".

REMOTE TEMPERATURE MONITORING APPARATUS AND TECHNIQUE

FIELD OF THE INVENTION

This application is a Rule 60 continuation of Parent application Ser. No. 299,966 filed Jan. 19, 1989, now abandoned.

The present invention relates to temperature monitoring apparatus and techniques using magnetic resonance generally.

BACKGROUND OF THE INVENTION

Temperature monitoring apparatus and techniques using magnetic resonance are known in the art.

Temperature measurements based on Nuclear Quadrupole Resonance (NQR) are described in the following references:

Yu. N. Bubkov, R. Sh. Lotfullin, R. V. Majera, and A. A. Buguslavskii—"Pulsed NQR thermometer for temperatures up to 870 degrees K.", Izvestiya Akademii Nank SSSR, Seriya F. Z. Cheskaya, Vol. 39, No. 12, 1975, pp. 2655–2660;

D. B. Utton, J. Vanier—"Thermometry by Nuclear Quadrupole Resonance", Instrumentation Technology, December 1976, pp. 47–52;

A. Ohte and H. Iwaaka—"A new nuclear quadrupole resonance standard thermometer" Temperature, American Institute of Physics, 1982, pp 1173–1180.

The essential feature of the NQR technique is measurement of temperature-dependent NQR frequencies which are an intrinsic property of the material used to construct an NQR sensor.

In laboratory contexts wherein various types of magnetic resonance were used to measure parameters of material structure, such as the lattice magnetic field, the temperature dependence of nuclear magnetic resonance (NMR) frequencies has been investigated. Reference is made in this context to S. Ogawa and S. Morimoto—"Nuclear Magnetic Resonance of $Fe^{57}$ in Various Ferromagnetic Oxides", Journal of the Physical Society of Japan, Vol. 17, No. 4, April 1962, pp 654–659. This reference shows, inter alia, at Tables I(a), I(b) and II, the relationship between internal magnetic field and temperature.

Thermometry systems in conventional use in clinical hyperthermia include probes employing thermocouples and thermistors having non-metallic output leads, so as not to interfere with the applied electromagnetic fields. Where multiple location temperature sensing is required, this is conventionally accomplished by moving the probe from location to location or by employing a plurality of such probes.

The state of the art in the use of thermometry systems in clinical hyperthermia is described in G. M. Samaras, A. Y. Cheung, "Microwave hyperthermia for cancer therapy", CRC Critical Reviews in Bioengineering, February, 1981, pp. 123–184. Some of the techniques described in the foregoing article are based on temperature dependence of optical parameters of given substances, such as GaAs, and liquid crystals. The advantages of such techniques are that output communication is provided by optical fiber leads, which do not interfere with the applied electromagnetic field. A multiple GaAs sensor is described in V. A. Vaguine, D. A. Christensen, J. H. Lindley, T. E. Walston, "Multiple sensor optical thermometry system for application in clinical hyperthermia", IEEE Transactions on Biomedical Engineering, Vol. BME-31, No. 1, January, 1984, pp 168–172.

The use of conventional thermometry systems in clinical hyperthermia provides relatively poor reproducibility over time and relatively poor spatial resolution, in view of the fact that the probes are inserted prior to each treatment. The use of conventional probes naturally involves very significant patient discomfort and is time intensive and costly.

A number of proposed methods of noninvasive thermometry are described in T. C. Cetas, "Will thermometric tomography become practical for hyperthermia treatment monitoring?", Cancer Research (SUPPL.) 44, October 1984, 4805s–4808s. The methods proposed therein all involve unsatisfactory compromises between reading rate, temperature sensitivity, spatial discrimination, stability and reproducibility.

It has been proposed to employ non-zero external static magnetic field NMR for directly measuring the temperature of living tissue in vivo in a clinical hyperthermia context. Such proposals are based on temperature dependence of NMR relaxation times and are described in the following publications:

D. L. Parker, "Application of NMR imaging in hyperthermia: an evaluation of the potential for localized tissue heating and noninvasive temperature monitoring", IEEE Transactions on Biomedical Engineering, Vol. BME-31, No. 1, January 1984, pp 161–167; and S. Peterson, J. Saaf, M. Bolmsjo, B. Persson, "Temperature mapping using an Ultra Lowfield MR scanner", Sixth Annual Meeting of Society of Magnetic Resonance in Medicine, Aug. 17–21, 1987, New York City, U.S.A.

If realized, the technique described in the preceding two publications would provide non-invasive direct measurement of temperature of living tissue. However, it would require expensive instrumentation which would have to be compatible with clinical hyperthermia apparatus. Moreover, the relaxation parameters are not uniform in different subjects. Therefore, in order to establish an absolute temperature output, a complicated calibration procedure would be required.

SUMMARY OF THE INVENTION

The present invention seeks to provide a relatively low cost, easy to use, wireless thermometry system which is useful, inter alia, in clinical hyperthermia.

There is thus provided in accordance with a preferred embodiment of the present invention a thermometry system comprising an implantable element having temperature dependent NMR properties, apparatus for applying an RF (radio frequency) electromagnetic field to the implantable element, and apparatus for sensing the temperature dependent NMR response of the implantable element and for providing an output indication of temperature of the implantable element.

There is also provided in accordance with a preferred embodiment of the present invention a technique for in vivo temperature measurement of tissue comprising the steps of:

implanting in living tissue an element having temperature dependent NMR properties, applying an RF field to the element;

sensing the temperature dependent NMR response of the element; and providing an output indication of temperature of the implantable element.

There is also provided in accordance with a preferred embodiment of the present invention a clinical hyperthermia system comprising apparatus for selectably heating tissue in vivo, apparatus for monitoring the temperature of the tissue including at least one implantable element having temperature dependent NMR properties, apparatus for applying an RF field to the implantable element, and apparatus for sensing the temperature dependent NMR response of the implantable element and for providing an output indication of temperature of the implantable element.

There is also provided in accordance with a preferred embodiment of the present invention a technique for localized heating of living tissue comprising the steps of:
 implanting in living tissue at least one element having temperature dependent NMR properties,
 selectably heating living tissue;
 applying an RF field to the element;
 sensing the temperature dependent NMR response of the element; and
 providing an output indication of temperature of the implantable element.

In accordance with an embodiment of the present invention, the implanted element may remain in the tissue over an extended period, such as weeks and months, over which multiple clinical hyperthermia treatments may occur.

Additionally the implanted element does not require calibration.

Further in accordance with an embodiment of the invention, where a plurality of implanted elements are employed, they may be constructed to have different nuclear magnetic resonance frequency ranges so as to enable simultaneous measurement of temperatures at multiple locations.

Additionally in accordance with a preferred embodiment of the invention, the step of selectably heating tissue in vivo comprises the step of applying an RF heating field thereto and the technique also comprises measuring the distribution of the RF heating field at an NMR resonance frequency of said at least one element.

In accordance with the foregoing embodiment of the invention, the apparatus for applying an RF field forms part of the apparatus for selectably heating tissue and the step of measuring the distribution of the RF heating field takes place at times other than those at which an RF heating field is applied in a time shared arrangement and at a different frequency than that of the RF heating field.

BRIEF DESCRIPTION OF THE DRAWINGS

The present invention will be understood and appreciated from the following detailed description, taken in conjunction with the drawings in which.

DETAILED DESCRIPTION OF A PREFERRED EMBODIMENT

Figure 1:
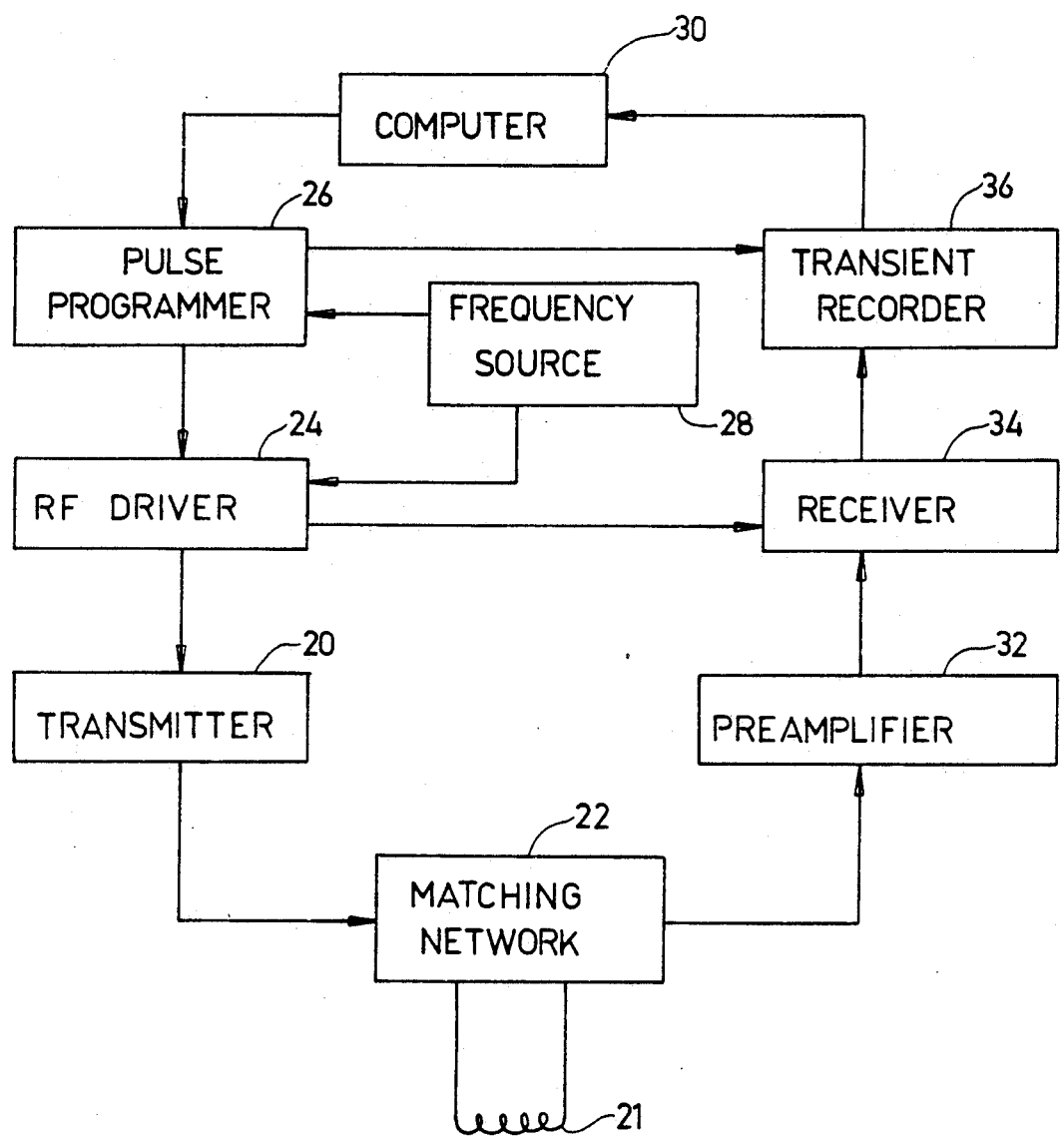
FIG. 1 is a block diagram illustration of a thermometry system constructed and operative in accordance with a preferred embodiment of the present invention.
Figure 1:
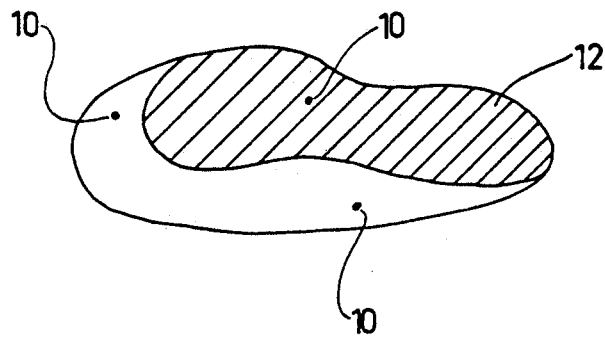

Reference is now made to FIG. 1, which illustrates a thermometry system constructed and operative in accordance with a preferred embodiment of the present invention. One or more implantable passive elements 10 having magnetic resonance properties, such as resonance frequency and NMR signal amplitude which have a known temperature dependency, are implanted in vivo in a living organism, such as the human body. The passive elements 10, which will be described hereinafter in greater detail, may be located in or near a tumor 12 or other body which is sought to be heated in a precisely controlled manner.

An RF transmitter 20, including a power amplifier such as a Model 200L manufactured by Amplifier Research of Souderton, Pa. 18964, U.S.A., provides an RF output via an antenna 21 and a matching network 22. The RF transmitter 20 receives a signal input from an RF driver 24, such as a Model 410, manufactured by Matec Instruments, Inc. of 60 Montebello Road, of Warwick, RI 02886, U.S.A., modified to operate at higher frequencies, which also receives inputs from a pulse programmer 26. Pulse programmer 26 includes a number of triggers, the timing of which is controlled by a computer 30, such as an IBM PC. The pulse programmer 26 and the RF driver 24 both receive a clocking input from a frequency source 28, such as a Model 5120A, manufactured by Wavetek San Diego Inc. of 9045 Balboa Ave. San Diego, Calif. 92122, U.S.A..

A preamplifier 32, such as a Model 254 manufactured by Matec, receives, via antenna 21 and matching network 22 magnetic resonance signals from elements 10, which contain temperature information. The preamplifier 32 provides an output to a receiver 34, such as a Model 615 manufactured by Matec, which also receives RF signal phase information from driver 24.

The receiver 34 provides an output to a transient recorder 36, such as a Gould Model 4035 which also receives timing information from pulse programmer 26. The output of transient recorder 36 is supplied to computer 30, which provides an output indication of the temperature at elements 10.

Elements 10 each include material such as iron garnet having the following chemical composition: $5Fe_2O_3 \cdot M_2O_3$, wherein M is a rare earth metal. The internal magnetic field which determines the resonance frequency can be controlled by using an appropriate rare earth metal. For example, if M is Yttrium, the resonance frequency of element 10 at about 30 degrees C. is approximately 53.578 MHz. The temperature dependence is about 60 KHz/degree C. when the resonance frequency can be determined with accuracy of about 1 KHz. This leads to temperature resolution which is much better than 0.1 degree C., which is ordinarily required for clinical hyperthermia. The above-cited reference to Ogawa et al shows, inter alia, at Tables I(a), I(b) and II, the known relationship between internal magnetic field and temperature.

Figure 2:
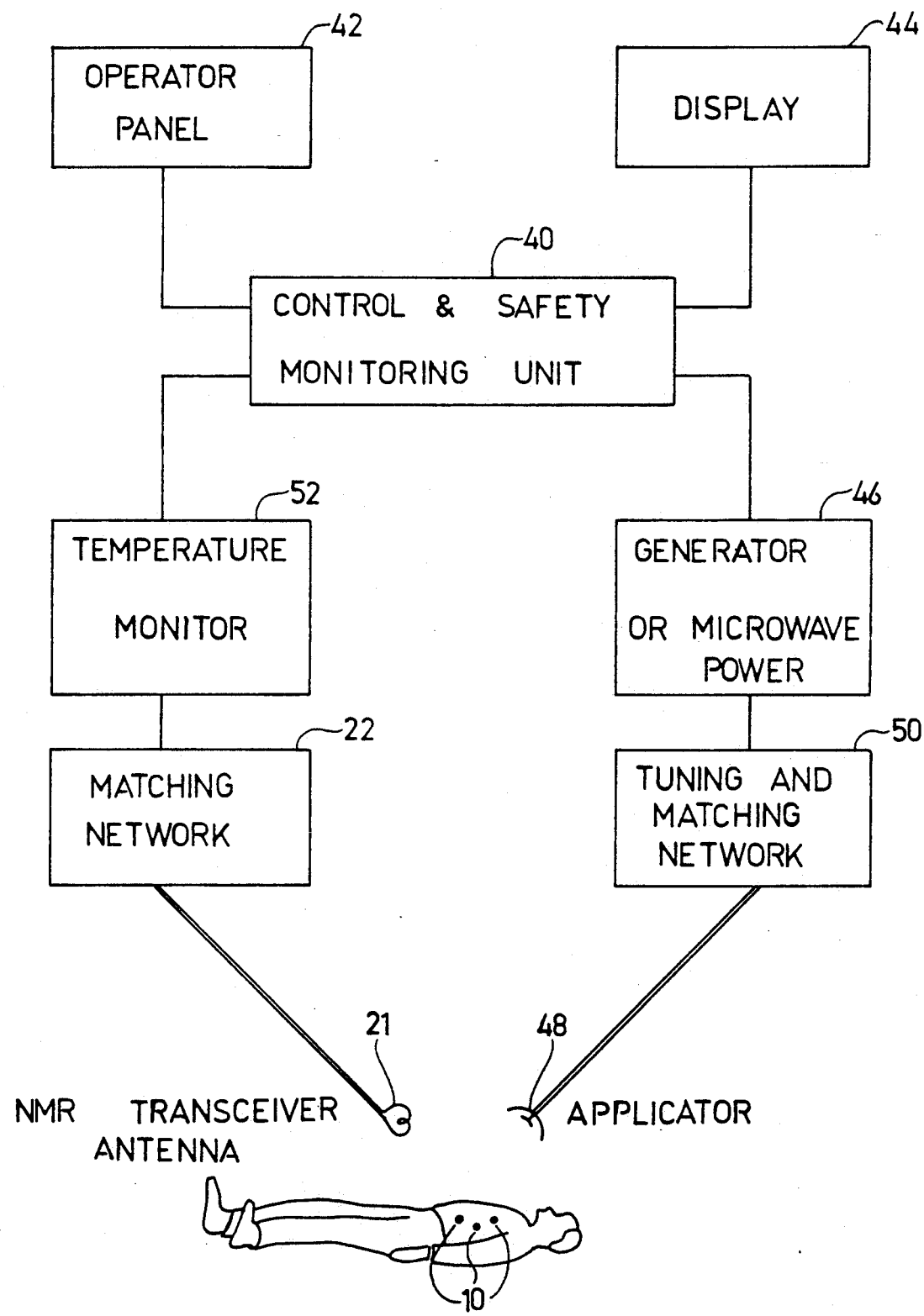
FIG. 2 is a block diagram illustration of clinical hyperthermia apparatus constructed and operative in accordance with a preferred embodiment of the invention.

Reference is now made to FIG. 2, which illustrates the thermometry system of the present invention in the context of a clinical hyperthermia system. A conventional clinical hyperthermia system such as model BSD-2000 manufactured by BSD Medical Corporation of 420 Chipeta Way, Salt Lake City, Utah 84108 USA, incorporates a control and safety monitoring unit 40, having an associated operator panel 42 and display 44.

Unit 40 operates a RF power generator 46, which alternatively could be a microwave power generator, which drives an applicator 48 via a tuning and matching network 50. The thermometry system of the present invention interfaces with the control and safety monitoring unit 40, and computer 30 (FIG. 1) or part thereof may be incorporated in unit 40. With the exception of all or part of computer 30 and the antenna and matching networks 21 and 22, the remainder of the system of FIG. 1 is shown as being incorporated in a temperature monitor 52.

Additionally in accordance with a preferred embodiment of the invention, the step of selectably heating tissue in vivo comprises the step of applying an RF heating field thereto and the technique also comprises measuring the distribution of the RF heating field at an NMR resonance frequency of said at least one element.

In accordance with the foregoing embodiment of the invention, the apparatus for applying an RF field forms part of the apparatus for selectably heating tissue, i.e. the same antenna may be used as the transceiver antenna 21 and the applicator 48, and the step of measuring the distribution of the RF heating field takes place at times other than those at which an RF heating field is applied in a time shared arrangement and at a different frequency than that of the RF heating field.

It will be appreciated by persons skilled in the art that the present invention is not limited by what has been particularly shown and described hereinabove. Rather the scope of the present invention is defined only by the claims which follow:

We claim:

1. A technique for in vivo temperature measurement of tissue comprising the steps of:
    locating in living tissue at least one element having a temperature dependent internal magnetic field;
    applying an RF field to the at least one element;
    sensing the temperature dependent internal magnetic field of said at least one element by sensing the nuclear magnetic resonance frequency thereof in response to the application of said RF field thereto; and
    providing an output indication of temperature of at least one element as a function of the sensed nuclear magnetic resonance frequency.

2. A technique according to claim 1 and wherein said element remains located in the tissue over an extended period, over which multiple clinical hyperthermia treatments may occur.

3. A technique for localized heating of living tissue comprising the steps of:
    implanting in living tissue at least one element having a temperature dependent internal magnetic field, selectably heating living tissue;
    applying an RF field to the at least one element;
    sensing the temperature dependent nuclear magnetic resonance frequency of the element; and
    providing an output indication of temperature of the implantable element, in order to monitor the heating of the living tissue and to enable prevention of overheating thereof.

4. A technique according to claim 3 and wherein said at least one implanted element may remain in the tissue over an extended period, over which multiple clinical hyperthermia treatments may occur.

5. A technique according to claim 3 and wherein said implanting and sensing steps include the steps of implanting a plurality of elements at multiple locations, each having a different nuclear magnetic resonance frequency range and simultaneously measuring of temperatures at said multiple locations by sensing the internal magnetic field thereof in response to an applied RF field having frequencies at said different frequency ranges.

6. A clinical hyperthermia system comprising:
    means for selectably heating tissue in vivo; and
    means for monitoring the temperature of the tissue, thereby to prevent overheating of said tissue, said means for monitoring including:
    at least one in vivo locatable element having a temperature dependent internal magnetic field;
    means for applying an RF field to the in vivo locatable element; and
    means for sensing the temperature dependent nuclear magnetic resonance frequency of said in vivo locatable element in response to the application of said RF field thereto and for providing an output indication of temperature of the locatable element as a function of the sensed nuclear magnetic resonance frequency.

7. A system according to claim 6 and wherein said at least one implantable element comprises iron garnet having the following chemical composition: $5Fe_2O_3 \cdot M_2O_3$, wherein M is a rare earth metal.

8. A system according to claim 6 and wherein said means for applying an RF field comprises a matching network and an RF antenna.

9. A system according to claim 6 wherein said means for selectably heating tissue in vivo comprises means for applying an RF heating field thereto.

* * * * *